United States Patent [19]

Di Fiore et al.

[11] 4,100,212
[45] Jul. 11, 1978

[54] PROCESS FOR CHLORINATING LINEAR PARAFFINS

[75] Inventors: Lucio Di Fiore; Benedetto Calcagno, both of Milan; Marcello Ghirga, Bresso, Milan, all of Italy

[73] Assignee: Societa'Italiana Resine S.p.A., Milan, Italy

[21] Appl. No.: 626,000

[22] Filed: Oct. 28, 1975

Related U.S. Application Data

[63] Continuation of Ser. No. 97,900, Dec. 14, 1970, abandoned.

[30] Foreign Application Priority Data

Dec. 23, 1969 [IT] Italy ............................... 26200 A/69

[51] Int. Cl.$^2$ ............................................. C07C 17/10
[52] U.S. Cl. .................................................... 260/660
[58] Field of Search ......................................... 260/660

[56] References Cited

U.S. PATENT DOCUMENTS 3,701,793   10/1972   Schmidt et al. ...................... 260/660

*Primary Examiner*—Delbert E. Gantz
*Assistant Examiner*—Joseph A. Boska
*Attorney, Agent, or Firm*—Sughrue, Rothwell, Mion, Zinn and Macpeak

[57] ABSTRACT

Liquid-phase chlorination of n-paraffins is improved as to yield on chlorine and as to restriction to mono-substitution by passing the paraffins up a reactor divided into stages by baffles and feeding chlorine in controlled amounts to each stage.

5 Claims, 1 Drawing Figure

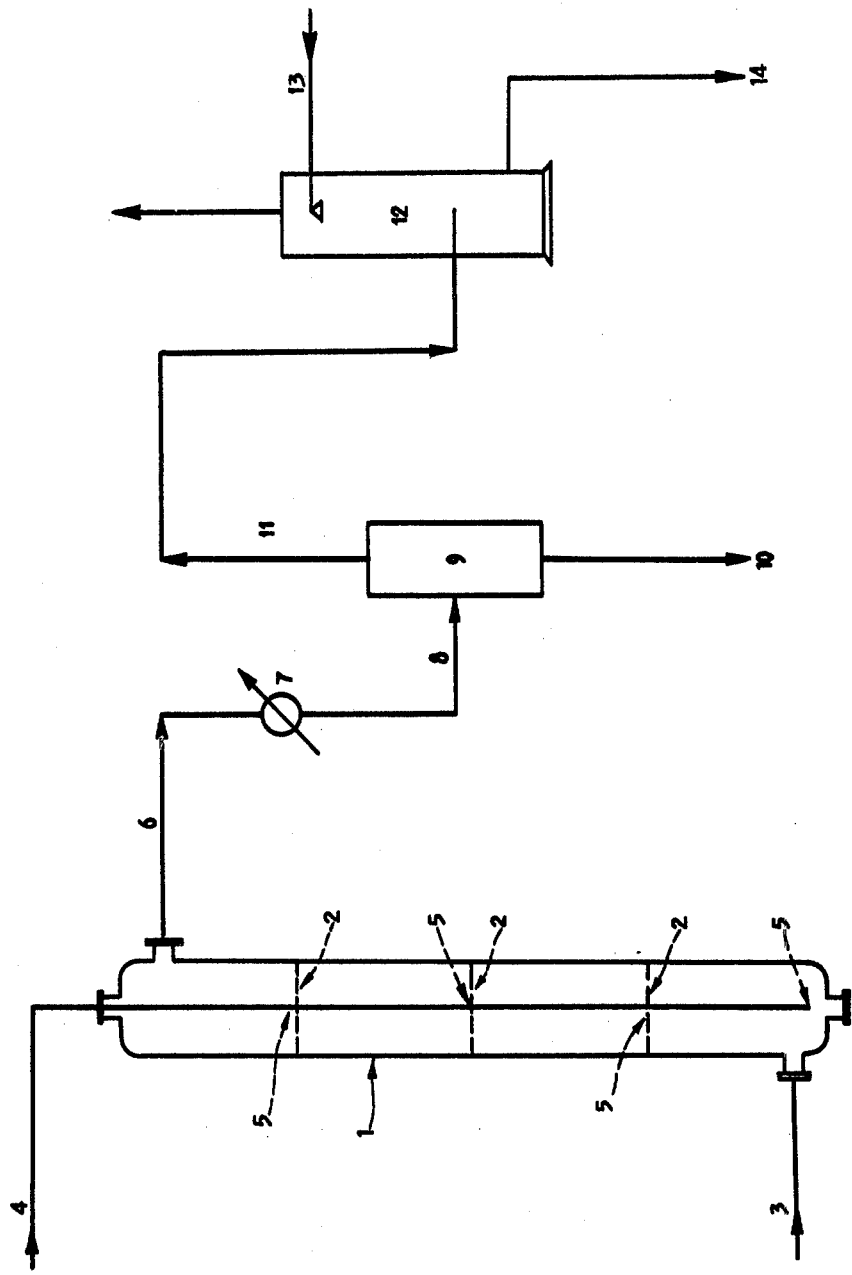

PROCESS FOR CHLORINATING LINEAR PARAFFINS

This is a continuation of application Ser. No. 97,900 filed Dec. 14, 1970 now abandoned.

The present invention relates to a process for the non-catalytic, continuous cycle liquid-phase chlorination of paraffins using gaseous chlorine.

From another aspect, the invention relates to a form of apparatus adapted to perform such chlorination.

More particularly, the invention describes a process for the chlorination of linear paraffins having from 9 to 15 or more carbon atoms in the molecule, under conditions which ensure a high yield of monochlorinated products.

Such products, as is well known, are used in industry for the synthesis of biodegradable detergents, by processes which provide for alkylation of benzene, followed by the fractional distillation of the products of alkylation.

In the said chlorination processes, it is essential to ensure the maximum yield of monochloro derivatives in view of economy of the process and of the undesired by-products which substances with a higher degree of chlorination produce during the following alkylation.

It is a fact known that such polychlorinates are converted into polyphenyl alkanes which are recovered as by-products of the alkylation reaction, together with polyalkyl benzenes. These latter are used in the manufacture of desirable additives for lubricating oils, but their properties and characteristic features are however jeopardised when polyphenyl alkanes are present to a relatively high extent.

It is well know that in processes of substitutive chlorination of hydrocarbons having a plurality of hydrogen atoms capable of replacement, there is a formation of polychlorinated derivatives in consecutive reaction, due to the action of the chlorine on the monohalogenated products.

In the production of chloroparaffins suitable for the manufacture of biodegradable detergents, therefore, it is important to ensure a formation of monochlorinated products as close as possible to the theoretical values, these values being dependent upon the proportion of paraffin:chlorine supplied.

However, the halogenation reaction described is one in which various other factors help to reduce the yield of monochloro derivatives. Thus, for example, the reagent mixture may include zones with a higher concentration of chlorine, in which products form which have an undesirably high degree of chlorination.

It is therefore necessary to achieve a rapid and efficient homogenisation of the liquid and gaseous reagents.

In the described processes, it is often difficult to achieve complete conversion of the chlorine even with relatively long contact times.

This fact is damaging both by reason of the loss of expensive reagent and because products of reaction result which are impaired by the presence of chlorine.

Therefore, one object of the present invention is a process for the non-catalytic continuous cycle liquid phase chlorination of linear paraffins with from 9 to 15 or more carbon atoms in the molecule, using gaseous chlorine, permitting the production of virtually theoretical quantities of monochloro derivatives.

A further object of the present invention is to provide a method of chlorinating the said paraffins which permits of virtually total conversion of the chlorine supplied.

A further object of the present invention is a form of apparatus suitable for the process of chlorinating the paraffins.

Further objects of the invention will become apparant from the following description.

The process of the present invention consists essentially in bringing the reagent liquid into contact with successive portions of gaseous chlorine in a plurality of stages of reaction which are in series inter se, each of the said stages providing essentially a homogeneous reaction mixture and being independent and communicating with the contiguous stages.

More precisely, according to the process of the present invention, in an elongated vertical tubular reactor, a plurality of reacting stages are established by means of appropriate baffles consisting of perforated sheets or plates. The liquid hydrocarbon is supplied totally and continuously to the base of the said reactor, while the gaseous chlorine is supplied at the bottom of each reaction stage, homogenously distributed throughout the cross-section of the reactor itself. For the purpose of the present invention, it is essential to work at a linear velocity of intake of gaseous chlorine into each reaction stage at values equal to or greater than 50 metres/sec. It is also essential for the proposed purposes that the velocity of gas passage from one stage to the other, through the baffles of the reactor, be maintained at levels equal to or greater than 2 cm/sec., such gases being normally constituted by hydrochloric acid alone, produced in the halogenation reaction. In particular, according to the process of the present invention, gaseous chlorine is supplied at the bottom of each reaction stage uniformly throughout the cross-section of the reactor, under conditions such that the linear velocity of the gas emerging from the distributor is between 50 and 150 metres/sec., these values being calculated under the operative conditions.

In practice, it has been found that optimum conditions are achieved in a system to which no external overpressure is applied, gaseous chlorine being supplied through tubular type, for example bayonet, distributors provided with holes of 0.5 to 2 mm. diameter.

In addition, the free section which allows passage of products from one stage to the next, and in particular the size of the holes in the baffles which define the various stages of the reactor, are so dimensioned as to ensure through said baffles a gas flow velocity of 2 to 60 cm/sec. and preferably of 3 to 15 cm/sec.

Proceeding according to the present invention achieves on the one hand a rapid and efficient blending of the liquid and gaseous reagents in each stage of reaction and on the other hand achieves a high degree of agitation of the reagent mixture due to the gaseous flow between the various stages of reaction.

Proceeding in this way avoids localised concentrations of chlorine which produce the undesired effects described previously.

According to the process of the present invention, a plurality of virtually independent stages of reaction are achieved in that, by the presence of the perforated baffles and proceeding under the conditions described, it is possible substantially to avoid the phenomena of blending reagent liquid in each stage with that of the preceding stages of reaction. In particular, at least two and preferably at least three independent reaction stages are achieved.

Even though the maximum number of such stages may be very large, it has been found in practice inadvisable to exceed approx. 12 such stages.

The best results are furthermore achieved by maintaining a proportion of height:diameter in each reaction stage, of between 1:1 to 5:1.

Thus, in carrying out the purposes of the present invention, linear paraffins having from 9 to 15 or more carbon atoms in the molecule are supplied to the base of a tubular reactor and caused to react with gaseous chlorine in a plurality of independent reaction stages.

In particular, the molar ratio of chlorine:paraffin supplied is kept between 0.1:1 and 5.0:1 and preferably 0.2:1 and 0.3:1, the chlorine, in the preferred form, being equally sub-divided into a number of streams equal to the number of reaction stages used. The rate of supply of the paraffins is furthermore maintained at values from 0.1 to 1.3 and preferably 0.4 to 1.0 volumes per volume of reactor and per hour.

The chlorination reaction is carried out at temperatures comprised between 90 and 170° C, the thermal effect of the reaction being controlled by means of heat exchangers positioned within the reactor. For the purpose, nests of tubes may be used, immersed in the reagent mixture, and containing circulating refrigerating fluid.

In the preferred embodiment, operation involves no overpressure being imposed on the chlorination reactor, even though it is possible to work at pressures below ambient pressure or at pressure levels up to a few atmospheres above atmospheric.

At the head of the chlorination reactor, finally, the products of chlorination are recovered and the liquid substances are separated from the gaseous.

The procedure described results in the production of chlorinated paraffins with a monochlorinated product content virtually equal to the theoretical values.

In addition, the process itself is simple and easy to control and permits of virtually total conversion of the chlorine supplied.

The process of the present invention has been described with particular reference to the monochlorination of linear paraffins having from 9 to 15 or more carbon atoms in the molecule. It is obvious, however, that this process can be applied to other thermal chlorinations of organic substances having a plurality of hydrogen atoms which can be substituted by chlorine atoms, when a controlled distribution of the halogen in the reaction products is required.

The experimental examples which follow will serve to provide further illustration of the invention, while in no way limiting its scope.

EXAMPLE 1

A series of n-decane chlorination tests were carried out in the laboratory apparatus shown diagrammatically in FIG. 1. In the diagram, reference numeral 1 denotes the chlorination reactor consisting of a glass column 100 mm. in diameter, 1500 mm. high and with an effective volume equal to approx. 10 litres.

This column is divided into four reaction stages of approx. equal volume, by the insertion of three perforated discs 2 made from Teflon.

The n-decane is supplied, after being preheated, to the foot of column 1, through the line 3.

The chlorine is supplied through the line 4 and introduced into the column 1 by means of a single monel alloy distributor with four holes 5 measuring 0.3 mm. in diameter, situated at different heights on the column 1, and intended to introduce chlorine into the bottom of each stage.

The product of reaction emerging at the top of the column 1 through the line 6 is cooled at 7 and supplied to the gas/liquid separator 9 through the line 8. Thus, the chlorinated product is recovered at 10 while the gas is passed through 11 to be distilled with water at 12.

In particular, water is supplied at 13 and the aqueous solution of hydrochloric acid is recovered through 14.

During the tests, a reaction temperature of 100 to 120° C was maintained, together with a throughput of chlorine of 40 to 140 g/litre of paraffin supplied and per hour, and a spatial velocity of paraffin of 0.25 to 0.5 volumes per volume of reactor per hour.

Any variation in the parameters of reaction was carried out at regular intervals of time, sufficiently long that in each case constant conditions of chlorination could be achieved. Table 1 summarises the results of three tests. More particularly shown are the percentage molar conversion rates of n-decane into the corresponding chlorinated products, the percentage yield in mols of monochloro derivatives based on converted substance and the corresponding theoretical yield. All the tests showed a virtually total conversion of the chlorine supplied.

Analytical determination of the chlorinated reaction products was carried out by means of gas chromatographic analysis.

Table 1

| Test No. | Molar conversion % | Yield in monochloro derivatives % | Theoretical yield |
|---|---|---|---|
| 1 | 24.24 | 83.38 | 83.76 |
| 2 | 29.06 | 80.00 | 80.26 |
| 3 | 39.35 | 72.47 | 72.44 |

EXAMPLE 2

In the chlorination of a mixture of linear paraffins having from 10 to 14 carbon atoms in the molecule, a metal reactor of tubular and elongated form was used, with a height of 6 m and a diameter of 0.8 metres. The reactor was divided into four stages of approx. equal volume, by means of three perforated plates.

At the bottom of the reactor and immediately above each perforated plate, there were gaseous chlorine distributors, of tubular shape, provided with holes having a diameter equal to 0.3 mm. Each stage was also provided with heat exchangers to control the exothermal nature of the reaction.

After preheating, 2.4 ou.m./hr. of linear paraffins were supplied to the bottom of the reactor and had the following composition expressed as percentages by weight, determined by gas chromatographic analysis.

| | |
|---|---|
| n-decane | 4.9% |
| n-undecane | 23.1% |
| n-dodecane | 53.8% |
| n-tridecane | 17.4% |
| n-tetradecane | 0.8% |

The chlorine was supplied at a rate of 70 nom.-cu.m./hr. approx., sub-divided into approx. equal quantities over the four distributors so as to achieve a linear inlet velocity equal to approx. 70 m/sec.

Chlorination was carried out at 115° C with a velocity of gas flow through the perforated plates ranging from approx. 4 cm/sec. between the first and second stages up to approx. 11 cm./sec. between the third and fourth stages. The products of reaction were discharged at the head of the reactor, after which the liquid products were separated from the gaseous products. Thus, a chlorinated paraffin was obtained having a chlorine content equal to approx. 5.8% by weight.

Such chloroparaffins were subjected to alkylation in excess benzene and in the presence of aluminium trichloride. After fractional distillation of the products of alkylation, 11 to 12 parts by weight of heavy by-products were obtained for every 100 parts by weight alkyl benzenes.

What we claim is:

1. A process for the non-catalytic continuous liquid-phase chlorination using gaseous chlorine of linear paraffins having 9 to 15 carbon atoms per molecule comprising:

contacting said gaseous chlorine and said linear paraffins in a reactor of an elongated tubular shape comprising a plurality of independent interconnecting reaction stages by means of baffles consisting of perforated sheets or plates in said reactor, each of said stages having a height to diameter ratio of 1:1 to 5:1, by supplying said paraffins to the base of said reactor and supplying gaseous chlorine through distributors at the bottom of each reaction stage at a linear inlet velocity of between 50 to 150 meters/sec. at a molar ratio of chlorine to paraffins of 0.1:1 to 5:1 and at a paraffins supply rate of 0.1 to 1.3 volumes of paraffins per reactor volume per hour, said chlorination reaction being carried out at temperatures from 90 to 170° C, the size of the holes in said baffles and said chlorination reaction conditions being carried out such that the gas velocity passing from one reaction stage to another, through the baffles, is between 2 and 60 cm/sec., said chlorination reaction being controlled at said temperatures using heat exchangers situated internally at each reaction stage; and recovering the reaction products at the head of the reactor.

2. A process according to claim 1, characterised in that the gaseous chlorine is supplied at the bottom of each reaction stage through distributors provided with holes of 0.5 to 2 mm. diameter.

3. A process according to claim 1, characterised in that the gas velocity from one stage to another is 3 to 15 cm/sec.

4. A process according to claim 1, characterised in that three to twelve reaction stages are provided in the chlorination reactor.

5. A process according to claim 1, characterised in that the molar ratios of supply are between 0.2:1 and 0.3:1.

* * * * *